US012638393B2

(12) United States Patent
James et al.

(10) Patent No.: US 12,638,393 B2
(45) Date of Patent: May 26, 2026

(54) PLASMONIC-SENSOR SYSTEM ATTACHMENT TO SMARTWATCH

(71) Applicants:Jay James, Berkeley, CA (US); Jeffrey Scott Crosby, Richmond, CA (US)

(72) Inventors: Jay James, Berkeley, CA (US); Jeffrey Scott Crosby, Richmond, CA (US)

(73) Assignee: Picoyune, LLC, Berkeley, CA (US)

( * ) Notice: Subject to any disclaimer, the term of this patent is extended or adjusted under 35 U.S.C. 154(b) by 622 days.

(21) Appl. No.: 18/071,604

(22) Filed: Nov. 29, 2022

(65) Prior Publication Data

US 2023/0168194 A1      Jun. 1, 2023

Related U.S. Application Data

(60) Provisional application No. 63/283,993, filed on Nov. 29, 2021, provisional application No. 63/283,989, filed on Nov. 29, 2021.

(51) Int. Cl.
| | |
|---|---|
| *G01N 21/55* | (2014.01) |
| *A61B 5/00* | (2006.01) |
| *G01N 21/552* | (2014.01) |

(52) U.S. Cl.
CPC ........... *G01N 21/554* (2013.01); *A61B 5/681* (2013.01)

(58) Field of Classification Search
CPC .......... G01N 21/554; G01N 2201/0221; A61B 5/681
See application file for complete search history.

(56) References Cited

U.S. PATENT DOCUMENTS

| | | | | |
|---|---|---|---|---|
| 2012/0052246 A1* | 3/2012 | Odom | ................... | B82Y 30/00 428/156 |
| 2017/0370836 A1* | 12/2017 | Gerion | ................... | G01N 21/82 |

FOREIGN PATENT DOCUMENTS

| | | | | | |
|---|---|---|---|---|---|
| EP | 3121587 A1 * | 1/2017 | ........... | G01N 21/554 |

* cited by examiner

*Primary Examiner* — Michelle M Iacoletti
*Assistant Examiner* — Mohamed Doumbia
(74) *Attorney, Agent, or Firm* — Jeffery Frazier

(57) ABSTRACT

Embodiments are disclosed of an analyte detection system configured as an attachment to a smartwatch. The detection-system hardware can comprise, for example, a plasmonic sensor configured to attach to, and align with the smartwatch's optics (e.g., LED and detector).

9 Claims, 3 Drawing Sheets

PLASMONIC-SENSOR SYSTEM ATTACHMENT TO SMARTWATCH

CROSS-REFERENCE TO RELATED APPLICATIONS

This application claims the benefit of priority from U.S. Provisional Patent Application No. 63/283,993 filed Nov. 29, 2021, and U.S. Provisional Patent Application No. 63/283,989 filed Nov. 29, 2021; each of which is incorporated herein by reference in its entirety.

FIELD

The present teachings relate to an analyte detection system configured as an attachment to a smartwatch.

INTRODUCTION

Smart devices, such as watches and phones, have become widely used throughout the world in recent years. Contemporary smart devices are analogous to minicomputers with internal memory, high quality cameras and light sources, powerful processors, robust operating systems, and wireless communications capabilities. Accordingly, such devices provide opportunities for advancing analytical sensing systems and their applications.

SUMMARY

An exemplary and non-limiting summary of various embodiments is set forth next.

Various aspects of the present teachings relate to the detection of analytes in a portable system that leverages various components and capabilities found in many contemporary smart devices, such as watches, phones, tablets, and the like. In various embodiments, for example, portable systems of the present teachings employ localized surface plasmon resonance (LSPR) sensors configured as attachment to a smart watch.

Plasmonic analyte sensing apparatus and methods suitable for use herein are described, for example, in U.S. patent application Ser. No. 17/197,805 filed Mar. 10, 2021 (Published as US 2021-0190683 A1); U.S. Pat. Nos. 10,976,252; 10,620,122; and U.S. Provisional Patent Application No. 62/653,555 filed Apr. 5, 2018; each of which is incorporated herein by reference in its entirety.

The attachment integrates a plasmonic sensor with biomonitoring optics disposed on the back of the smartwatch. The sensor uses a plasmonic film that selectively adsorbs a target and responds with changes in optical extinction. The change in extinction can be monitored optically with the smartwatch optoelectronics.

In general, commercially available smartwatches comprising integrated LEDs and photodiodes can be appropriate for monitoring the plasmonic signal. Software provided on the smart device (e.g., watch/smartphone) can process the data and provide a graphic user interface to relay results to the user.

BRIEF DESCRIPTION OF THE DRAWINGS

Various embodiments of the disclosure will be discussed with reference to the following exemplary and non-limiting drawings, in which like elements are numbered similarly, and where.

DETAILED DESCRIPTION

Reference will now be made to various embodiments. While the present teachings will be described in conjunction with various embodiments, it will be understood that they are not intended to limit the present teachings to those embodiments. On the contrary, the present teachings are intended to cover various alternatives, modifications, and equivalents, as will be appreciated by those of skill in the art.

According to various embodiments, the attachment integrates a plasmonic sensor with biomonitoring optics disposed on the back of the smartwatch. The sensor uses a plasmonic film that selectively adsorbs a target and responds with changes in optical extinction. The change in extinction can be monitored optically with the smartwatch optoelectronics. In accordance with various embodiments, the present teachings contemplate utilizing smartwatches comprising integrated LEDs and photodiodes for monitoring the plasmonic signal. Software provided on the smart device (e.g., watch/smartphone) can process the data and provide a graphic user interface to relay results to the user.

According to various embodiments, the sensor hardware can comprise a plasmonic sensor configured to attach to, and align with a smartwatch's optics (e.g., LED and detector).

In various embodiments, the plasmonic sensor can take a variety of forms, depending on the application. According to various embodiments, for example, the plasmonic film can comprise a substantially 2-dimensional array of metal nanomaterial, e.g., gold nanoparticles. In accordance with various embodiments, depending on the target of the test, the plasmonic film can be functionalized to selectively adsorb the target from solution.

In various embodiments, changes in the extinction of the light as it passes through the plasmonic film, between the source (LED in smartwatch) and detector (photodiode in smartwatch), can comprise the signal used to detect or quantify the target species.

In some embodiments, the sensor can include a fluid handling system to transport sample and/or other test media across the plasmonic film.

In various embodiments, the plasmonic films in the attachment are replaceable.

In accordance with various embodiments, the plasmonic signal can be monitored during and/or after exposure to the sample.

According to various embodiments, the plasmonic sensor can include an optical cavity to increase the number of film transits between source and detector, thereby increasing the sensitivity of the LSPR test system (See, e.g., U.S. patent application Ser. No. 18/071,597, co-filed on Nov. 29, 2022; incorporated herein by reference.)

According to various embodiments, the smartwatch can be held in place magnetically or mechanically. In various embodiments, the attachment can work with the smartwatch removed from the wrist and placed on the attachment, where the attachment can function as a stand.

Figure 1:
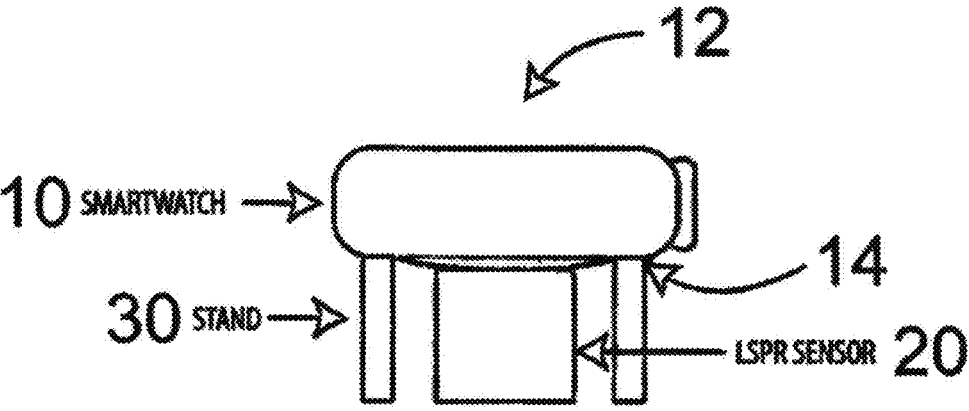
FIG. 1 is a schematic side view of an LSPR sensor attached to a smartwatch, including a stand for holding the LSPR sensor and smartwatch together in a suitable configuration facilitating interoperability between their respective subsystems, according to various embodiments of the present teachings.
Figure 2:
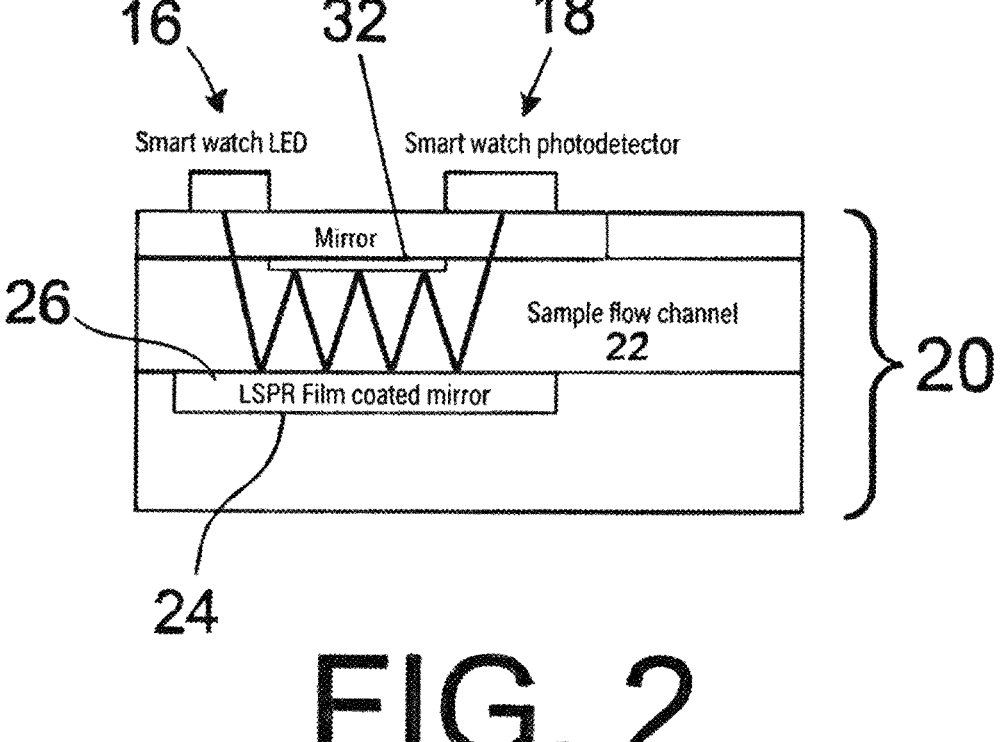
FIG. 2 is a schematic side sectional view showing features of the LSPR sensor and smartwatch of FIG. 1 that can function together in use/operation, according to various embodiments of the present teachings.

An exemplary portable analyte detection system, according to the present teachings, is illustrated in FIGS. 1 and 2. A smartwatch 10 comprises a watch face 12 and an opposing backside 14. A light source 16 and a photodetector 18 are disposed at respective, spaced-apart positions on the backside. An attachment body 20 comprises a sample flow channel 22, a mirrored substrate 24 disposed on one side of the sample flow channel 22, and an LSPR film 26 on a side of the mirrored substrate 24 facing into the sample flow channel 22; wherein the attachment body 20 can be fit against the backside 12 of the smartwatch 10 such that the light source 16 can direct a beam of light across the sample flow channel 22 to the LSPR film 26, which beam can then be reflected back across the channel 22 by the mirrored substrate 24.

According to various embodiments, a stand 30 is configured to support and align the smartwatch 10 on top of the attachment body 20 for sample analysis.

In various embodiments, a mirror 32 is disposed along the backside 14 of the smartwatch 10, between the light source 16 and the photodetector 18, and opposing the mirrored substrate 24 across the sample flow channel 22, whereby an optical cavity is formed along the region between the mirror 32 and the mirrored substrate 24.

According to various embodiments, the attachment body further comprises a fluid handling system (not shown) for transporting test media across the LSPR film.

Figure 3:
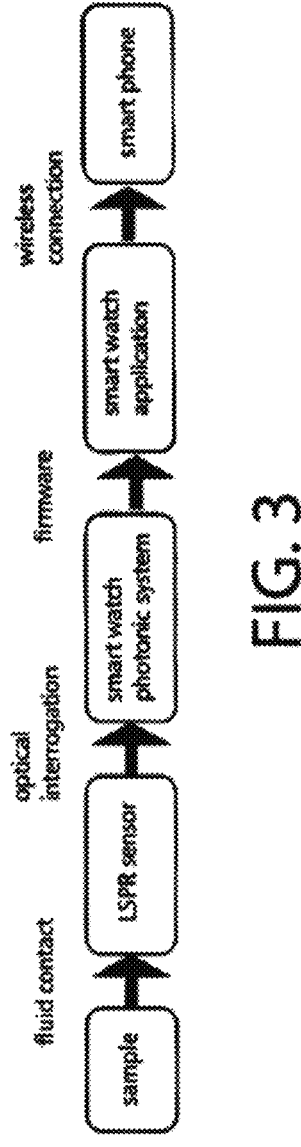
FIG. 3 is a flow diagram illustrating features/systems of an LSPR sensor/smart device combination, such as illustrated in FIGS. 1 and 2, utilized at each step of a workflow testing for the presence of an analyte in a sample and presenting results to a user, according to various embodiments of the present teachings.

FIG. 3 is a flow diagram illustrating features/systems of an LSPR sensor/smart device combination, such as illustrated in FIGS. 1 and 2, utilized at each step of a workflow testing for the presence of an analyte in a sample and presenting results to a user, according to various embodiments of the present teachings.

According to various embodiments, the sensor system can collect digital signal from the smartwatch optoelectronics, analyze the data, and report results to the user.

According to various embodiments, the sensor of the present teachings can be used, for example, in a temperature cycle. The signal comprises an LSPR signal of change in the transmission of the light through the nanoparticle film. A temperature cycle is employed to compare the LSPR signal after sampling in comparison to the signal with the analyte desorbed from the film through heating.

All references set forth herein are expressly incorporated by reference in their entireties for all purposes.

Those skilled in the art can now appreciate from the foregoing description that the broad teachings herein can be implemented in a variety of forms. Therefore, while the present teachings have been described in connection with various embodiments and examples, the scope of the present teachings are not intended, and should not be construed to be, limited thereby. Various changes and modifications can be made without departing from the scope of the present teachings.

It is claimed:

1. A portable analyte detection system, comprising:
a smartwatch comprising a watch face and an opposing backside;
a light source and a photodetector disposed at respective, spaced-apart positions on the backside;
an attachment body comprising a sample flow channel, a mirrored substrate disposed on one side of the sample flow channel, and an LSPR film on a side of the mirrored substrate facing into the sample flow channel; wherein the attachment body can be fit against the backside of the smartwatch such that the light source can direct a beam of light across the sample flow channel to the LSPR film, which beam can then be reflected back across the channel by the mirrored substrate.

2. The system of claim 1, further comprising a stand configured to support and align the smartwatch on top of the attachment body for sample analysis.

3. The system of claim 1, wherein the LSPR film comprises a substantially two-dimensional array of metal nanomaterial.

4. The system of claim 3, wherein the metal nanomaterial comprises a plurality of gold nanoparticles.

5. The system of claim 1, wherein the LSPR film is functionalized to selectively adsorb a target analyte from solution.

6. The system of claim 1, further comprising a mirror disposed along the backside of the smartwatch, between the light source and the photodetector, and opposing the mirrored substrate across the sample flow channel, whereby an optical cavity is formed along the region between the mirror and the mirrored substrate.

7. The system of claim 1, wherein the attachment body further comprises a fluid handling system for transporting test media across the LSPR film.

8. The system of claim 1, wherein the smartwatch comprises a processor and computer code executable by the processor for collecting and analyzing data.

9. The system of claim 1, further comprising a smart phone comprising a wireless radio configured for receiving wireless data transmissions from a wireless radio of the smartwatch, whereby LSPR test results can be wirelessly transmitted from the smartwatch to the smart phone for display to a user on a graphical user interface of the phone.

\* \* \* \* \*